(12) United States Patent
Lin et al.

(10) Patent No.: US 10,005,823 B2
(45) Date of Patent: Jun. 26, 2018

(54) PEPTIDES HAVING EFFECTS ON PROMOTING WOUND HEALING, COLLAGEN PRODUCTION, ANGIOGENESIS, ACTIVATION OF IMMUNOCYTES AND APPLICATIONS THEREOF

(71) Applicant: TCI Co., Ltd, Taipei (TW)

(72) Inventors: Yung-Hsiang Lin, Taipei (TW); Chin-Hsiu Yu, Taipei (TW); Yun-Ching Tsai, Taipei (TW); Ciao-Ting Chen, Taipei (TW); Hsiang-Ling Su, Taipei (TW)

(73) Assignee: TCI CO., LTD, Tai Pei (TW)

( * ) Notice: Subject to any disclaimer, the term of this patent is extended or adjusted under 35 U.S.C. 154(b) by 0 days. days.

(21) Appl. No.: 15/336,212

(22) Filed: Oct. 27, 2016

(65) Prior Publication Data
US 2017/0121378 A1 May 4, 2017

(30) Foreign Application Priority Data

Oct. 28, 2015 (TW) .............................. 104135487 A (51) Int. Cl.
*A61K 38/00* (2006.01)
*C07K 14/46* (2006.01)
*A23L 33/10* (2016.01)
*A61K 9/48* (2006.01)
*A61K 9/20* (2006.01)
*A61K 9/28* (2006.01)

(52) U.S. Cl.
CPC ............ *C07K 14/461* (2013.01); *A23L 33/10* (2016.08); *A23V 2002/00* (2013.01); *A61K 9/20* (2013.01); *A61K 9/28* (2013.01); *A61K 9/48* (2013.01); *A61K 38/00* (2013.01)

(58) Field of Classification Search
None
See application file for complete search history.

(56) References Cited

U.S. PATENT DOCUMENTS

| | | | | |
|---|---|---|---|---|
| 8,298,548 | B2 * | 10/2012 | Avila | A61K 8/975 424/195.17 |
| 8,349,799 | B1 * | 1/2013 | Sung | A61K 9/5161 514/12.1 |
| 2011/0269667 | A1 * | 11/2011 | Shoseyov | A61K 38/39 514/1.8 |

* cited by examiner

*Primary Examiner* — Marcela M Cordero Garcia
(74) *Attorney, Agent, or Firm* — Muncy, Geissler, Olds & Lowe, PC (57) ABSTRACT

The present invention provides 11 peptides represented as SEQ ID NO: 1-11. The peptides have the ability of anti-virus and bacteria, and can reduce infections, clean necrotic tissue, and promote debridement so as to facilitate wound healing. Moreover, the peptides can also induce collagen secretion and activate fibroblasts and keratinocytes so as to stimulate angiogenesis. Thus, the peptides of the present invention are suitable for development as a health caring product to help an individual enhance recovery and immunity.

6 Claims, 7 Drawing Sheets

FIG. 7

PEPTIDES HAVING EFFECTS ON PROMOTING WOUND HEALING, COLLAGEN PRODUCTION, ANGIOGENESIS, ACTIVATION OF IMMUNOCYTES AND APPLICATIONS THEREOF

CROSS-REFERENCE TO RELATED APPLICATION

This application claims the priority of Taiwanese patent application No. 104135487, filed on Oct. 28, 2015, which is incorporated herewith by reference.

BACKGROUND OF THE INVENTION

1. Field of the Invention

The present invention relates generally to a peptide, and more particularly, to provide a peptide having effects on promoting wound healing, collagen production, angiogenesis, activation of immunocytes.

2. The Prior Arts

After injury and surgery, most patients need a long time and certain food to recovery wound and energy. In early rehabilitation of patients, it is common method to get the proper foods, nutrients and drug which can help them heal fast and efficiently form injury.

SUMMARY OF THE INVENTION

As such, the present invention provides an effective peptide selected from the group consisting of SEQ ID NO:1-SEQ ID NO:11, and validates the effective peptides having the ability of promoting wound healing, collagen production, angiogenesis, activation of immunocytes.

A primary objective of the present invention is to provide a method for promoting wound healing, collagen production, angiogenesis, activation of immunocytes in a subject in need thereof, comprising administering to the subject an effective amount of a peptide, wherein the peptide is selected from the group consisting of SEQ ID NO:1 to SEQ ID NO:11 or a combination thereof.

Another objective of the present invention is to provide a method for increasing the mRNA levels of interleukin-1β (IL-1β) and tumor necrosis factor-α (TNF-α) in a cell, comprising contacting the cell with an effective amount of a peptide, wherein the peptide is selected from the group consisting of SEQ ID NO:1 to SEQ ID NO:11 or a combination thereof.

A further objective of the present invention is to provide a composition comprising: a core comprising a peptide; and a layer of natural polymeric material enveloping the core, wherein the peptide is selected from the group consisting of SEQ ID NO:1 to SEQ ID NO:11 and a combination thereof.

According to an embodiment of the present invention, the peptide activates the mRNA levels of interleukin-1β (IL-1β).

According to an embodiment of the present invention, the peptide activates the mRNA levels of tumor necrosis factor-α (TNF-α).

According to an embodiment of the present invention, the cell is an infected cell or inflamed cell, and the cell is obtained from a wound tissue, an inflamed tissue or an infected tissue.

According to an embodiment of the present invention, the core further comprises an additive or pharmacological acceptable excipient, and the additive is citric acid, taurine, vitamins, pantothenic acid or nicotinic acid According to an embodiment of the present invention, the composition is in the form of tablet.

According to an embodiment of the present invention, the composition is filled in a capsule.

According to an embodiment of the present invention, the composition is used as a food or pharmaceutical composition.

Accordingly, the present invention provides some embodiments to validate that the peptides can induce interleukin-1β (IL-1β) and tumor necrosis factor-α (TNF-α) overexpression to have the ability of anti-virus and bacteria, reduce infections, clean necrotic tissue, and promote debridement so as to facilitate wound healing. And other embodiments also validate that the peptides can induce interleukin-8 (IL-8) and chemokine (C-X-C motif) ligand 12 (CXCL12) overexpression to circulate immune cells to appear in the wound and active immune cells; still other embodiments also validate that the peptides can induce interleukin-10 (IL-10) down-expression to promote fibrous tissue to secrete collagen so as to facilitate wound repair and healing. The present invention further provides some embodiments to validate that the peptides can induce IL-1β and TNF-α overexpression to activate fibroblasts and keratinocyte so as to stimulate angiogenesis.

According to the effect of the peptides, the present invention further provides a method for promoting wound healing, collagen production, angiogenesis, activation of immunocytes in a subject in need thereof, comprising administering to the subject an effective amount of the peptides.

BRIEF DESCRIPTION OF THE DRAWINGS

The present invention will be apparent to those skilled in the art by reading the following detailed description of a preferred embodiment thereof, with reference to the attached drawings, in which.

DETAILED DESCRIPTION OF THE PREFERRED EMBODIMENT

The accompanying drawings are included to provide a further understanding of the invention, and are incorporated in and constitute a part of this specification. The drawings illustrate embodiments of the invention and, together with the description, serve to explain the principles of the invention.

In the present embodiment is to obtain the peptides of the bass extract. First, a prepared bass sample is treated with acid solution and extracted with water to obtain a bass mixture; then, the bass mixture is digested with enzyme complex to obtain a digested product; finally, the digested product is filtered and purified to obtain the peptides of the present invention. The examples below show the sequences of the peptides and its effects, the present invention is described in detail below.

Example 1

Preparation of Bass Extract

First, cutting a bass into about 2 to 6 cm in size with slicer as raw material, wherein the bass comprises fish skin, scales, bone and meat. And washing the raw material with 2 to 5-fold of reverse osmosis (RO) water for 2 to 3 times to remove blood and impurities, obtaining a prepared bass sample.

Then, treating the prepared bass sample with an acid solution at a ratio of 1:5 (w/v), wherein the concentration of the acid solution is 1% to 5% hydrochloric acid, sulfuric acid or phosphoric acid. Soaking the acid treated bass sample in 15° C. to 20° C. for 10 to 48 hr, and washing the acid treated bass sample with 2 to 5-fold of RO water for 2 to 3 times to remove the acid solution, finally adjusting the pH value between 4 and 8 with calcium carbonate to obtain a bass mixture.

After preparing the bass mixture, extracting the bass mixture with 55° C. to 100° C. hot water for 1 to 6 hr to obtain an extracted bass mixture; centrifuging the extracted bass mixture at 3000 rpm for 10 min and filtering the impurities. Purifying the extracted bass mixture with 0.2% to 1% calcium carbonate or limestone, then filtering the extracted bass mixture with 1 to 10 µm filter membrane and ion exchange resin column to remove impurities and limestone, further, to isolate and purify an effective peptide from the extracted bass mixture. Treating the effective peptide with activated carbon to deodorize and decolorize, and concentrating the effective peptide under reduce pressure to a volume of 1/10 to 1/20 at 50° C. to 60° C.

Next, digesting the effective peptide with an enzyme complex at 40° C. to 60° C. for 1 to 5 hr to obtain a digested product, wherein the enzyme complex comprises 0.01% to 0.1% keratinase and bromelain, 0.1% to 5% papain, trypsin, pepsin, alcalase, neutrase, protamex and flavourzyme. After digesting, denaturing the enzyme in the digested product at 85° C. to 95° C. for 10 to 30 min, and cooling. Filtering the digested product with diatomaceous earth and activated carbon for two times; sterilizing the digested product with ultra-high temperature (UHT) at 135° C. to 140° C. for 3 to 5 sec; and filtering the digested product with 0.2 µm filter membrane to sterilize and remove small impurities, further, to obtain the peptides of the bass extract in the present invention.

Example 2

The Sequence of the Peptides of the Bass Extract

After appropriate dilution, the peptides of the bass extract are centrifuged at 13,000 rpm for 2 min to obtain 200 µL supernatant. The supernatant is desalted and concentrated using C18-Zip Tip (MILLPORE, MA) and dissolved in water taking a half volume to perform multiple LC-MS/MS analysis. All MS/MS spectra are processed using Mascot Distiller and database search is performed by Mascot Search engine.

Reaction condition:
Mass Spectrometer: LTQ XL (Thermo Scientific)
LC system: Agilent 1200 Series
Buffer A: ddH$_2$O/0.1% formic acid
Buffer B: 100% ACN/0.1% formic acid
Analytical column: C18 reverse phase column

TABLE 1

Gradient table

| Time (min) | B % |
|---|---|
| 0.00 | 5 |
| 10.02 | 5 |
| 10.05 | 5 |
| 45.00 | 40 |
| 50.00 | 85 |
| 60.00 | 85 |
| 63.00 | 5 |
| 75.02 | 5 |
| 75.05 | 5 |
| 90.00 | 5 |

After sequencing these peptides, there are 11 peptides in the bass extract, as shown in Table 2.

TABLE 2

The sequence of the peptides of the bass extract

| SEQ ID | Sequence |
|---|---|
| SEQ ID NO: 1 | VPGPMGPMGPRGPPGPSGSPGPQG |
| SEQ ID NO: 2 | VPGPMGPMGPRGPPGPS |
| SEQ ID NO: 3 | VPGPMGPMGPRGPPGPSGS |
| SEQ ID NO: 4 | ISVPGPMGPM |
| SEQ ID NO: 5 | VPGPMGPMGPRGPPGPSGSPGPQG |
| SEQ ID NO: 6 | VPGPMGPMGPRGPPGPSGS |
| SEQ ID NO: 7 | PGSSGEQGAPGPSGPAGPRGPPGS SGSTGKDGVNGLPGPIGPPGPRGR NGDV |
| SEQ ID NO: 8 | PAGNVGAPGPKGTRGAAG |
| SEQ ID NO: 9 | PQMSYGYDEKSAGISVPGPMGPM |
| SEQ ID NO: 10 | GSTGESGRPGEPGLPGA |
| SEQ ID NO: 11 | GAPGF |

Example 3

The Gene Expression of Immunocytes

Human monocytic (THP-1) cells are cultured in 6-well plate (5×10$^5$), and separated into 4 groups, each experimental group is treated with lipopolysaccharide (LPS) for LPS induced inflammation model, as shown in Table 3.

TABLE 3

The treatment and reaction time of each group

| Group | Treatment | Reaction Time |
|---|---|---|
| Control group | No | No |
| LPS comparable group | LPS | 27 hr, 9 hr, 6 hr |
| The peptides of the bass extract (low concentration) | 1% peptides of the bass extract + LPS | THP-1 cells are induced by LPS prior to the peptides treatment (3 hr minimum), and THP-1 cells are treated with the peptides of the bass extract for 24 hr, 6 hr and 3 hr, respectively. |
| The peptides of the bass extract (High concentration) | 2% peptides of the bass extract + LPS | THP-1 cells are induced by LPS prior to the peptides treatment (3 hr minimum), and THP-1 cells are treated with the peptides of the bass extract for 24 hr, 6 hr and 3 hr, respectively. |

Collecting THP-1 cells with different treatment and reaction time, extracting RNA of THP-1 cells using RNA isolation kit (GeneMark), reverse transcribing RNA to cDNA using Transcriptor First Strand cDNA Synthesis Kit (Roche), detect target gene using SYBR Green Master Mix (KAPA), and analyzing the gene expression using Step One Software (Applied Biosystems) to identify the impact and effect of the peptides of the bass extract on the immunocytes, which are shown in FIG. 1 to FIG. 7.

Figure 1:
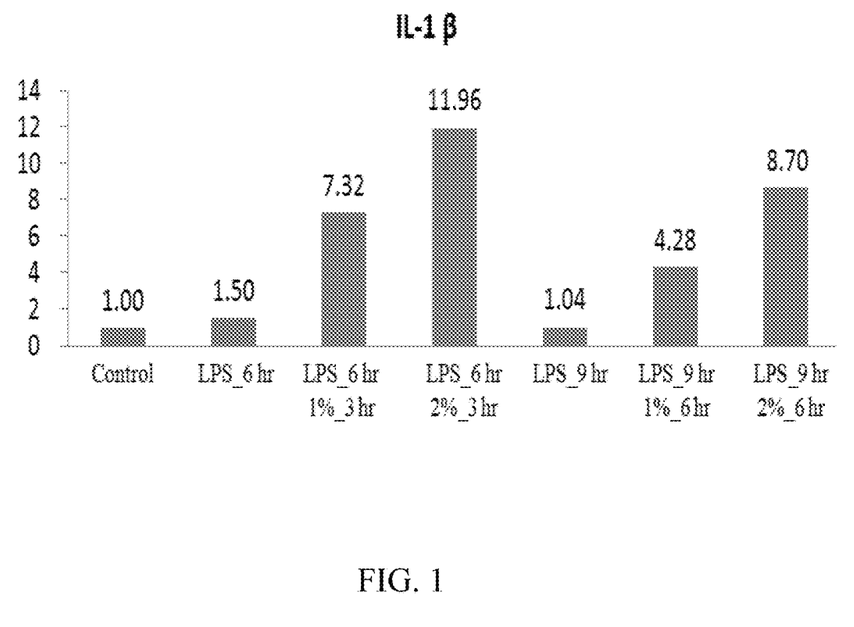
FIG. 1 is a histogram illustrating the effect of the peptides of the bass extract on interleukin-1β (IL-1β) mRNA expression in LPS induced inflammation model.

Referring to FIG. 1, there is shown a histogram illustrating the effect of the peptides of the bass extract on interleukin-1β (IL-1β) mRNA expression in LPS induced inflammation model. As show in FIG. 1, IL-1β mRNA expression in THP-1 cells induced by LPS is increased. In LPS induced inflammation for 6 hr model, IL-1β mRNA expression in THP-1 cells treated with 1% and 2% respectively the peptides of the bass extract for 3 hr is increased 4.8 and 7.9 fold compared to control group (LPS_6 hr); in LPS induced inflammation for 9 hr model, IL-1β mRNA expression in THP-1 cells treated with 1% and 2% respectively the peptides of the bass extract for 6 hr is increased 4.3 and 8.7 fold compared to control group (LPS_9 hr).

Figure 2:
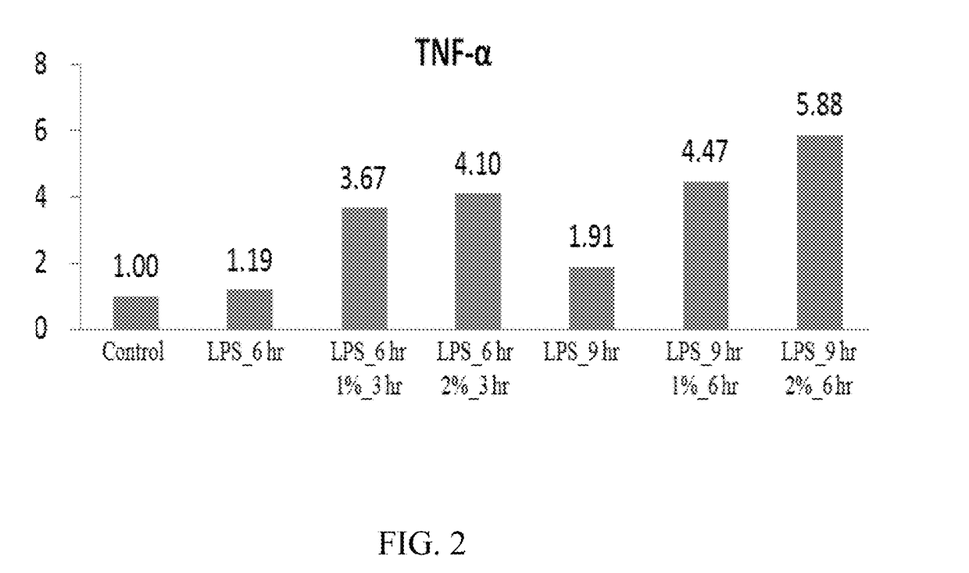
FIG. 2 is a histogram illustrating the effect of the peptides of the bass extract on tumor necrosis factor-α (TNF-α) mRNA expression in LPS induced inflammation model.

Referring to FIG. 2, there is shown a histogram illustrating the effect of the peptides of the bass extract on tumor necrosis factor-α (TNF-α) mRNA expression in LPS induced inflammation model. As show in FIG. 2, TNF-α mRNA expression in THP-1 cells induced by LPS is increased. In LPS induced inflammation for 6 hr model, TNF-αmRNA expression in THP-1 cells treated with 1% and 2% respectively the peptides of the bass extract for 3 hr is increased 3 and 3.5 fold compared to control group (LPS_6 hr); in LPS induced inflammation for 9 hr model, IL-1β mRNA expression in THP-1 cells treated with 1% and 2% respectively the peptides of the bass extract for 6 hr is increased 2.3 and 4 fold compared to control group (LPS_9 hr). IL-1β and TNF-α overexpression are important mediators of inflammation to have the ability of anti-virus and bacteria, to reduce infections, clean necrotic tissue, and to promote debridement so as to facilitate wound healing.

Figure 3:
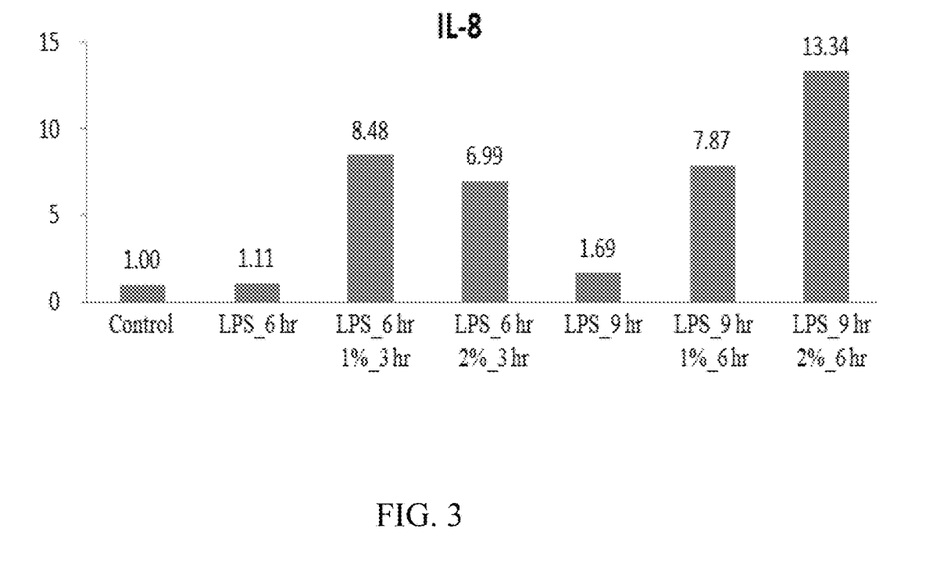
FIG. 3 is a histogram illustrating the effect of the peptides of the bass extract on interleukin-8 (IL-8) mRNA expression in LPS induced inflammation model.

Referring to FIG. 3, there is shown a histogram illustrating the effect of the peptides of the bass extract on interleukin-8 (IL-8) mRNA expression in LPS induced inflammation model. As show in FIG. 3, IL-8 mRNA expression in THP-1 cells induced by LPS is increased. In LPS induced inflammation for 6 hr model, IL-8 mRNA expression in THP-1 cells treated with 1% and 2% respectively the peptides of the bass extract for 3 hr is increased 7.6 and 6.3 fold compared to control group (LPS_6 hr); in LPS induced inflammation for 9 hr model, IL-8 mRNA expression in THP-1 cells treated with 1% and 2% respectively the peptides of the bass extract for 6 hr is increased 4.7 and 7.9 fold compared to control group (LPS_9 hr).

Figure 4:
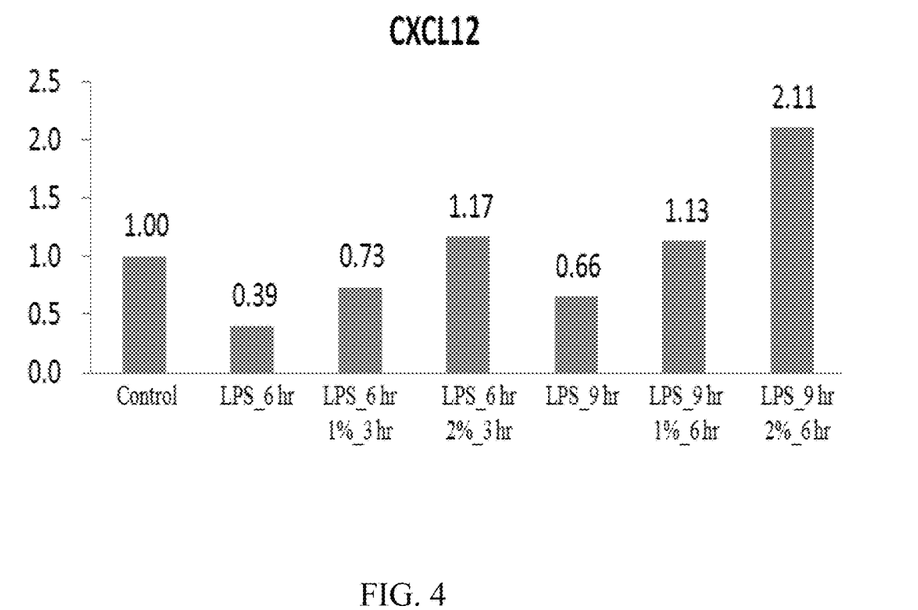
FIG. 4 is a histogram illustrating the effect of the peptides of the bass extract on chemokine (C-X-C motif) ligand 12 (CXCL12) mRNA expression in LPS induced inflammation model.

Referring to FIG. 4, there is shown a histogram illustrating the effect of the peptides of the bass extract on chemokine (C-X-C motif) ligand 12 (CXCL12) mRNA expressions in LPS induced inflammation model. As show in FIG. 4, CXCL12 mRNA expression in THP-1 cells induced by LPS is increased. In LPS induced inflammation for 6 hr model, CXCL12 mRNA expression in THP-1 cells treated with 1% and 2% respectively the peptides of the bass extract for 3 hr is increased 1.9 and 3 fold compared to control group (LPS_6 hr); in LPS induced inflammation for 9 hr model, CXCL12 mRNA expression in THP-1 cells treated with 1% and 2% respectively the peptides of the bass extract for 6 hr is increased 1.7 and 3.2 fold compared to control group (LPS_9 hr). IL-8 and CXCL12 overexpression can stimulate immune system circulating immune cells to appear in the wound and active immune cells.

Figure 5:
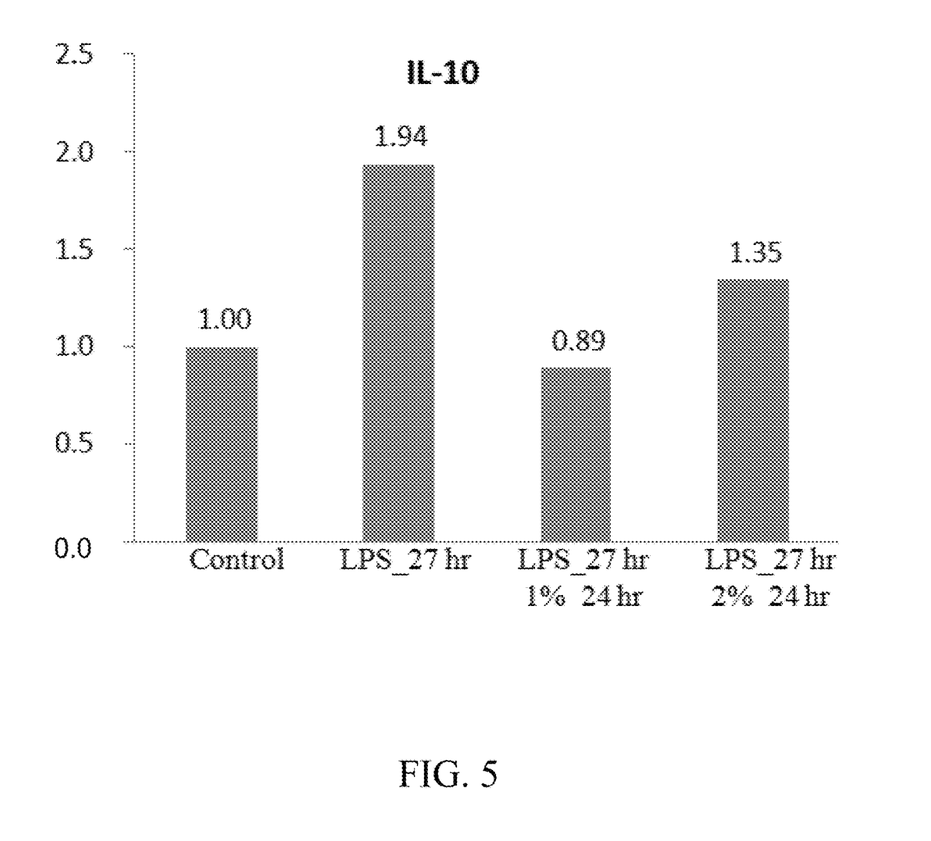
FIG. 5 is a histogram illustrating the effect of the peptides of the bass extract on interleukin-10 (IL-10) mRNA expression in LPS induced inflammation model.

Referring to FIG. 5, there is shown a histogram illustrating the effect of the peptides of the bass extract on interleukin-10 (IL-10) mRNA expression in LPS induced inflammation model. As show in FIG. 5, IL-10 mRNA expression in THP-1 cells induced by LPS is decreased. In LPS induced inflammation for 27 hr model, IL-10 mRNA expression in THP-1 cells treated with 1% and 2% respectively the peptides of the bass extract for 24 hr is decreased 54% and 30% compared to control group (LPS_27 hr). IL-10 downexpression can promote fibrous tissue to secrete collagen so as to facilitate wound repair and healing.

Figure 6:
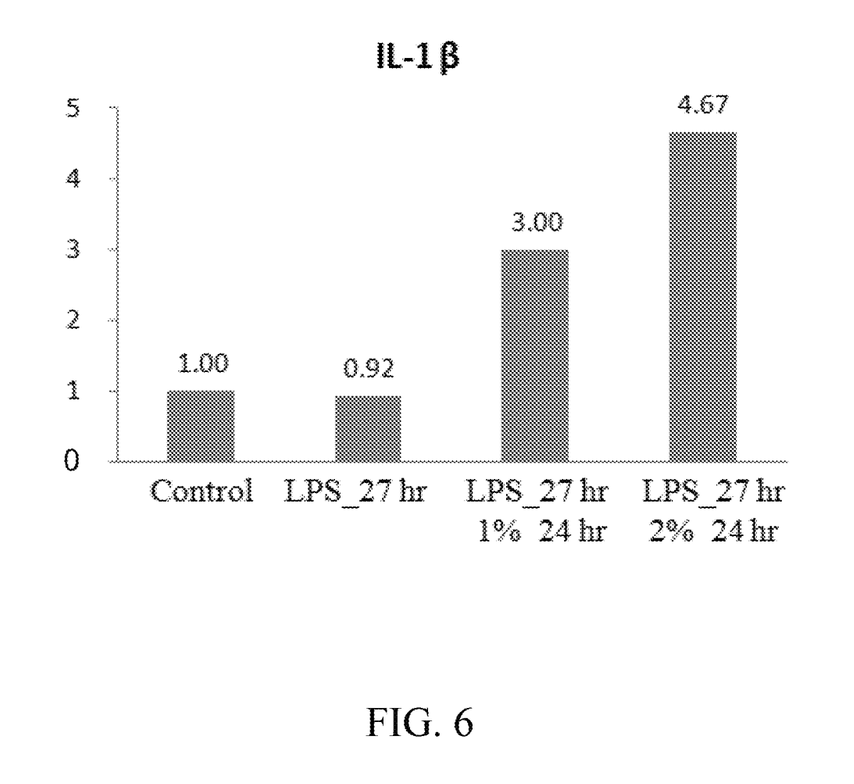
FIG. 6 is a histogram illustrating the effect of the peptides of the bass extract on IL-1β mRNA expression in LPS induced inflammation model.
Figure 7:
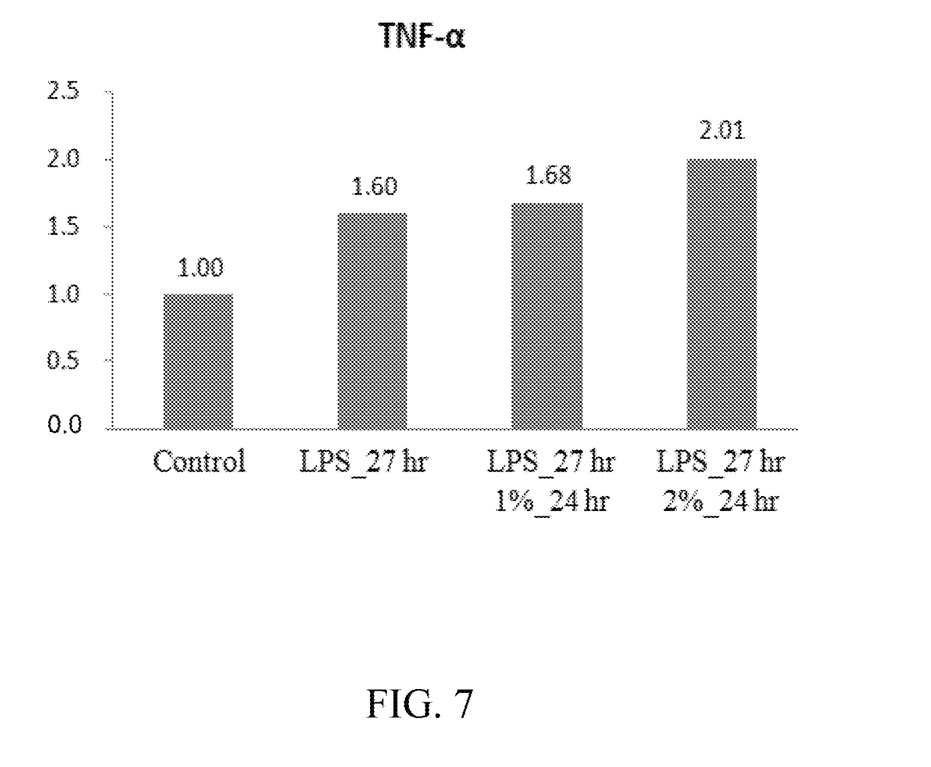
FIG. 7 is a histogram illustrating the effect of the peptides of the bass extract on TNF-α mRNA expression in LPS induced inflammation model.

Referring to FIGS. 6 and 7, there are shown histograms illustrating the effect of the peptides of the bass extract on IL-1β and TNF-α mRNA expressions in LPS induced inflammation model. As show in FIG. 6, IL-1β mRNA expression in THP-1 cells induced by LPS is increased. In LPS induced inflammation for 27 hr model, IL-1β mRNA expression in THP-1 cells treated with 1% and 2% respectively the peptides of the bass extract for 24 hr is increased 3.3 and 5.1 fold compared to control group (LPS_27 hr). As show in FIG. 7, TNF-α mRNA expression in THP-1 cells induced by LPS is increased. In LPS induced inflammation for 27 hr model, TNF-α mRNA expression in THP-1 cells treated with 2% the peptides of the bass extract for 24 hr is increased 2.3 fold compared to control group (LPS_27 hr). IL-1β and TNF-α overexpression can activate fibroblasts and keratinocyte to stimulate angiogenesis.

Therefore, according to above-mentioned the impact of IL-1β, TNF-α, IL-8, IL-10 and CXCL12 expressions in LPS induced inflammation model, which validates that the peptides of the present invention can circulate immune cells to appear in the wound and active immune cells, have the ability of anti-virus and bacteria, reduce infections, clean necrotic tissue, and promote debridement so as to facilitate wound healing. Also, the peptides of the present invention can promote fibrous tissue to secrete collagen so as to facilitate wound repair and healing. Additionally, IL-1β and TNF-α overexpression can activate fibroblasts and keratinocyte to stimulate angiogenesis.

According to the effect of the peptides, the present invention further provides a method for promoting wound healing, collagen production, angiogenesis, activation of immunocytes in a subject in need thereof, comprising administering to the subject an effective amount of the composition or stable aqueous composition containing the peptides. The composition or stable aqueous composition can be tablet, capsule, liquid, gel, slurry, suspension, power, dressing, lotion, spray and film, but not limited thereto.

Moreover, the composition comprising: a core comprising the peptides of the present invention; and a layer of natural polymeric material enveloping the core, wherein the core further comprises an additive or pharmacological acceptable excipient, and the additive is citric acid, taurine, vitamins, pantothenic acid or nicotinic acid. The stable aqueous composition comprising: the peptides of the present invention; and a solubilizing agent. The composition or stable aqueous composition further can be a food or pharmaceutical composition as a healthcare-related product, or be an external application as auxiliary product.

Although the present invention has been described with reference to the preferred embodiments thereof, it is apparent to those skilled in the art that a variety of modifications and changes may be made without departing from the scope of the present invention which is intended to be defined by the appended claims.

What is claimed is:

1. A method for promoting wound healing, collagen production, angiogenesis, activation of immunocytes in a subject in need thereof, comprising administering to the subject an effective amount of a peptide mixture, wherein the peptide mixture comprises SEQ ID NO:1, SEQ ID NO:2, SEQ ID NO:3, SEQ ID NO:4, SEQ ID NO: 7, SEQ ID NO: 8, SEQ ID NO: 9, SEQ ID NO: 10 and SEQ ID NO: 11.

2. The method according to claim 1, wherein the peptide mixture activates the mRNA levels of interleukin-1β (IL-1β).

3. The method according to claim 1, wherein the peptide mixture activates the mRNA levels of tumor necrosis factor-α (TNF-α).

4. A method for increasing the mRNA levels of interleukin-1β (IL-1β) and tumor necrosis factor-α (TNF-α) in a cell, comprising contacting the cell with an effective amount of a peptide mixture, wherein the peptide mixture is comprises SEQ ID NO:1, SEQ ID NO:2, SEQ ID NO:3, SEQ ID NO:4, SEQ ID NO: 7, SEQ ID NO: 8, SEQ ID NO: 9, SEQ ID NO: 10 and SEQ ID NO: 11.

5. The method according to claim 4, wherein the cell is an infected cell or inflamed cell.

6. The method according to claim 4, wherein the cell is obtained from a wound tissue, an inflamed tissue or an infected tissue.

* * * * *

SEQUENCE LISTING

```
<160> NUMBER OF SEQ ID NOS: 11

<210> SEQ ID NO 1
<211> LENGTH: 24
<212> TYPE: PRT
<213> ORGANISM: Lates calcarifer

<400> SEQUENCE: 1

Val Pro Gly Pro Met Gly Pro Met Gly Pro Arg Gly Pro Pro Gly Pro
1               5                   10                  15

Ser Gly Ser Pro Gly Pro Gln Gly
            20

<210> SEQ ID NO 2
<211> LENGTH: 17
<212> TYPE: PRT
<213> ORGANISM: Lates calcarifer

<400> SEQUENCE: 2

Val Pro Gly Pro Met Gly Pro Met Gly Pro Arg Gly Pro Pro Gly Pro
1               5                   10                  15

Ser

<210> SEQ ID NO 3
<211> LENGTH: 19
<212> TYPE: PRT
<213> ORGANISM: Lates calcarifer

<400> SEQUENCE: 3

Val Pro Gly Pro Met Gly Pro Met Gly Pro Arg Gly Pro Pro Gly Pro
1               5                   10                  15

Ser Gly Ser

<210> SEQ ID NO 4
<211> LENGTH: 10
<212> TYPE: PRT
<213> ORGANISM: Lates calcarifer

<400> SEQUENCE: 4

Ile Ser Val Pro Gly Pro Met Gly Pro Met
1               5                   10

<210> SEQ ID NO 5
<211> LENGTH: 24
<212> TYPE: PRT
<213> ORGANISM: Lates calcarifer

<400> SEQUENCE: 5

Val Pro Gly Pro Met Gly Pro Met Gly Pro Arg Gly Pro Pro Gly Pro
1               5                   10                  15

Ser Gly Ser Pro Gly Pro Gln Gly
            20
```

-continued

```
<210> SEQ ID NO 6
<211> LENGTH: 19
<212> TYPE: PRT
<213> ORGANISM: Lates calcarifer

<400> SEQUENCE: 6

Val Pro Gly Pro Met Gly Pro Met Gly Pro Arg Gly Pro Pro Gly Pro
1               5                   10                  15

Ser Gly Ser

<210> SEQ ID NO 7
<211> LENGTH: 52
<212> TYPE: PRT
<213> ORGANISM: Lates calcarifer

<400> SEQUENCE: 7

Pro Gly Ser Ser Gly Glu Gln Gly Ala Pro Gly Pro Ser Gly Pro Ala
1               5                   10                  15

Gly Pro Arg Gly Pro Pro Gly Ser Ser Gly Ser Thr Gly Lys Asp Gly
                20                  25                  30

Val Asn Gly Leu Pro Gly Pro Ile Gly Pro Pro Gly Pro Arg Gly Arg
            35                  40                  45

Asn Gly Asp Val
    50

<210> SEQ ID NO 8
<211> LENGTH: 18
<212> TYPE: PRT
<213> ORGANISM: Lates calcarifer

<400> SEQUENCE: 8

Pro Ala Gly Asn Val Gly Ala Pro Gly Pro Lys Gly Thr Arg Gly Ala
1               5                   10                  15

Ala Gly

<210> SEQ ID NO 9
<211> LENGTH: 23
<212> TYPE: PRT
<213> ORGANISM: Lates calcarifer

<400> SEQUENCE: 9

Pro Gln Met Ser Tyr Gly Tyr Asp Glu Lys Ser Ala Gly Ile Ser Val
1               5                   10                  15

Pro Gly Pro Met Gly Pro Met
                20

<210> SEQ ID NO 10
<211> LENGTH: 17
<212> TYPE: PRT
<213> ORGANISM: Lates calcarifer

<400> SEQUENCE: 10

Gly Ser Thr Gly Glu Ser Gly Arg Pro Gly Glu Pro Gly Leu Pro Gly
1               5                   10                  15

Ala

<210> SEQ ID NO 11
<211> LENGTH: 5
<212> TYPE: PRT
<213> ORGANISM: Lates calcarifer
```

-continued

```
<400> SEQUENCE: 11

Gly Ala Pro Gly Phe
1               5
```